(12) United States Patent
Gellert

(10) Patent No.: US 9,201,050 B2
(45) Date of Patent: Dec. 1, 2015

(54) METHOD FOR IMPROVING A CHROMATOGRAPHIC DETECTION LIMIT FOR AN ANALYTE

(75) Inventor: Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 896 days.

(21) Appl. No.: 13/390,885

(22) PCT Filed: Aug. 6, 2010

(86) PCT No.: PCT/EP2010/061510
§ 371 (c)(1),
(2), (4) Date: May 7, 2012

(87) PCT Pub. No.: WO2011/020722
PCT Pub. Date: Feb. 24, 2011

(65) Prior Publication Data
US 2012/0226445 A1    Sep. 6, 2012

(30) Foreign Application Priority Data
Aug. 19, 2009  (DE) .......................... 10 2009 038 112

(51) Int. Cl.
*G01N 30/00*  (2006.01)
*G01N 30/86*  (2006.01)

(52) U.S. Cl.
CPC ........ *G01N 30/8641* (2013.01); *G01N 30/8637* (2013.01); *G01N 2030/862* (2013.01)

(58) Field of Classification Search
CPC ....................... G01N 30/8641; G01N 30/8637
USPC .......................................................... 702/23
See application file for complete search history.

(56) References Cited

U.S. PATENT DOCUMENTS 7,219,038 B2 * 5/2007 Tracy et al. .................... 702/189
7,337,066 B2 * 2/2008 Neiss ................................ 702/8
(Continued)

FOREIGN PATENT DOCUMENTS

GB       2 329 475      3/1999
WO    WO 93/21592    10/1993

OTHER PUBLICATIONS

Statistik Bachelor-Kurs Nachweis-, Erfassungs- und Bestimmungsgrenze nach DIN 32 645 K. Molt (17 pages).
(Continued)

*Primary Examiner* — Sujoy Kundu
*Assistant Examiner* — Ricky Ngon
(74) *Attorney, Agent, or Firm* — Cozen O'Connor

(57) ABSTRACT

A method for improving the chromatographic detection limit for an analyte including a) producing a chromatogram with a peak of the analyte, b) calculating a regression straight line for a baseline from measured values of a section without a peak in the chromatogram, c) calculating a regression function from measured values of the peak of the analyte, d) subtracting the regression function from the chromatogram, e) calculating a regression polynomial for the baseline from the values of the chromatogram which have been changed in step d), f) calculating a further regression function from the measured values of the peak in the produced chromatogram, g) calculating a peak area between the regression polynomial and the further regression function, h) repetition of step d) with the further regression function instead of the regression function and of steps e), f) and g), until the calculated peak area changes by less than a predetermined amount.

1 Claim, 3 Drawing Sheets

(56) References Cited

U.S. PATENT DOCUMENTS

2008/0128607 A1* 6/2008 Herold et al. ............... 250/282
2010/0292957 A1* 11/2010 Satulovsky ................. 702/179

OTHER PUBLICATIONS

Deutsche Norm Nachweis-, Erfassungs- und Bestimmungsgrenze (10 pages).

Volkmar Neitzel; Bestimmungsgrenze ist nicht gleich Bestimmungsgrenze (pp. 248-251).

Gan F. et al: "Baseline correction by improved iterative polynomial fitting with automatic threshold", Chemometrics and Intelligent Laboratory Systems; Bd. 82, No. 1-2; XP024894964 (pp. 59-65).

Raso M. A. et al: "A General Fitting Program for Resolution of Complex Profiles II. Automatic Baseline Correction", Computers& Chemistry; Bd. 15, No. 1, 1991, XP002609779 (pp. 29-35).

David A., Mc Nulty, Halliday J. H. Macfie: "The Effect of Different Baseline Estimators on the Limit of Quantificaton in Chromatography", Journal of Chemometrics, Bd. 11, 1997, XP002609780 (pp. 1-11).

* cited by examiner

METHOD FOR IMPROVING A CHROMATOGRAPHIC DETECTION LIMIT FOR AN ANALYTE

CROSS-REFERENCE TO RELATED APPLICATIONS

This is a U.S. national stage of application No. PCT/EP2010/061510 filed 6 Aug. 2010. Priority is claimed on German Application No. 10 2009 038 112.0 filed 19 Aug. 2009, the content of which is incorporated herein by reference in its entirety.

BACKGROUND OF THE INVENTION

1. Field of the Invention

The invention relates to chromatography and, more particularly, to a method for improving the chromatographic detection limit for an analyte.

2. Description of the Related Art

In chromatography, a sample of a substance mixture to be analyzed is guided through a chromatographic separation apparatus. As a result of the different rates of movement through the separation apparatus, the analytes, i.e., the individual substances of the substance mixture, reach the outlet of the separation apparatus at different times and are detected there in succession by a suitable detector. As a measured signal, the detector produces a chromatogram, which consists of a baseline and a number of peaks corresponding to the separated substances. In practice, the chromatogram is noisy, with the individual peaks protruding more or less clearly from the signal noise. The noise corresponds to the difference between the greatest and smallest measured value in a considered section of the chromatogram without a peak, e.g., the two portions in front of and behind the peak of interest.

By way of example, the noise can also be defined as n-times the standard deviation of the measured values from their mean. The detection limit of an analyte is defined as k-times, e.g., 2-times, the noise of the baseline; i.e., the peak height measured from the noise-free baseline, i.e., from the mean of the noise, must be at least k-times the noise. In the case of well-resolved peaks, the peak area above the noise-free baseline is proportional to the concentration of the analyte, with the peak area, unlike the peak height, providing exact results even in the case of unsymmetrical peaks.

Thus, the level of the detection limit for an analyte is dependent on the accuracy with which the noise-free baseline can be established in the region of the peak of the analyte.

SUMMARY OF THE INVENTION

It is an object of the invention to improve the establishment of a noise-free baseline and thus improve the level of a detection limit of an analyte.

This and other objects and advantages are achieved in accordance with the invention by a method comprising a) producing a chromatogram with a peak of the analyte, b) calculating a regression line for a baseline (zero line) from measured values of a section in the chromatogram without a peak, c) calculating, by a processor, a regression function, consisting of a Gaussian function and the regression line, from measured values of the peak of the analyte, d) subtracting the regression function from the chromatogram, e) calculating, by the processor, a regression polynomial for the baseline from the values of the chromatogram modified in step d), f) calculating, by the processor, a further regression function, consisting of the Gaussian function and the regression polynomial, from the measured values of the peak in the produced chromatogram, g) calculating, by the processor, a peak area between the regression polynomial and the further regression function, h) repeating step d), with the further regression function in place of the regression function, and steps e), f) and g) until the calculated peak area changes by less than a preset amount.

The iterative method in accordance with the invention converges very rapidly and provides a very precise estimate of the noise-free baseline in the region of the peak of interest.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For a further explanation of the invention, the following text refers to the figures in the drawings, in which.

DETAILED DESCRIPTION OF THE PREFERRED EMBODIMENTS

Figure 1:
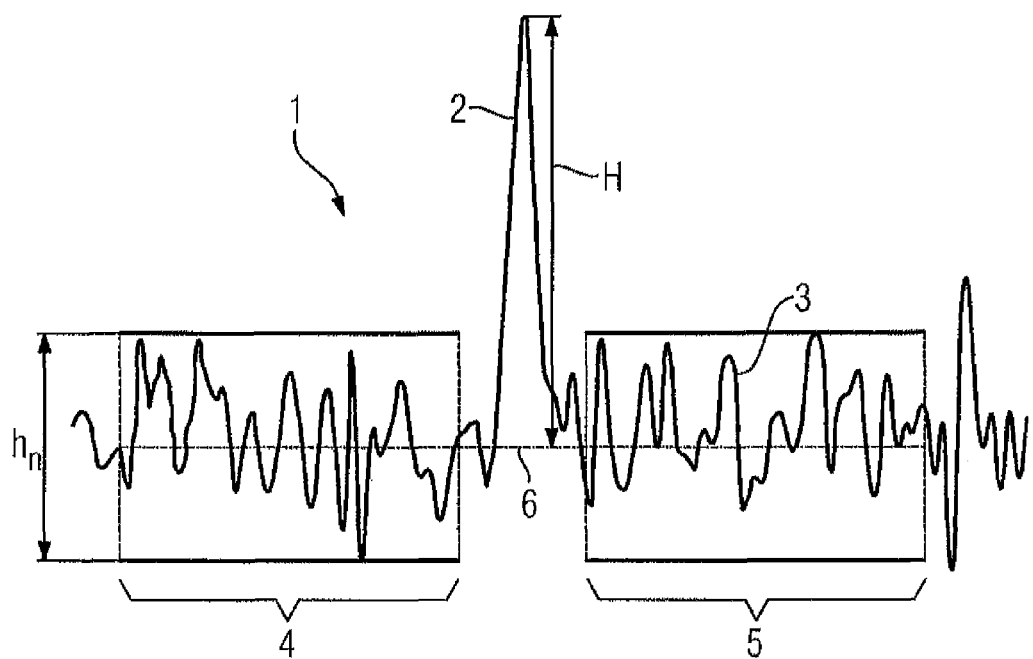
FIG. 1 shows an exemplary graphical plot of a chromatogram with a peak.

FIG. 1 shows a chromatogram 1 in the region of the peak 2 of an analyte of interest. The baseline (zero line) 3 of the chromatogram 1 is very noisy. In order to determine the noise, a section of the chromatogram 1 without a peak is considered in the vicinity of the peak 2, in this case, e.g., two portions 4 and 5 in front of and behind the peak 2 of interest, and the maximum variation $h_n$ of the baseline 3 is established in the two portions 4 and 5. The noise-free baseline 6, in a first approximation, emerges from the mean of the noise $h_n$. The peak height H is established from the noise-free baseline 6, with a peak height H being defined as the detection limit of the analyte, which corresponds to k-times, e.g., 2-times, the noise $h_n$. Finally, the peak area above the noise-free baseline 6 is calculated in a processor to determine the concentration of the analyte.

The factor k for the detection limit emerges from the uncertainty when establishing the noise-free baseline 6 in the region of the peak 2. The more precisely the noise-free baseline 6 can be established, the smaller the factor k can be selected and the lower the detection limit for the analyte is.

In the following text, an example is used to explain how the establishment of the baseline in the region of the peak 2 is improved with the method in accordance with the invention.

Figure 2:
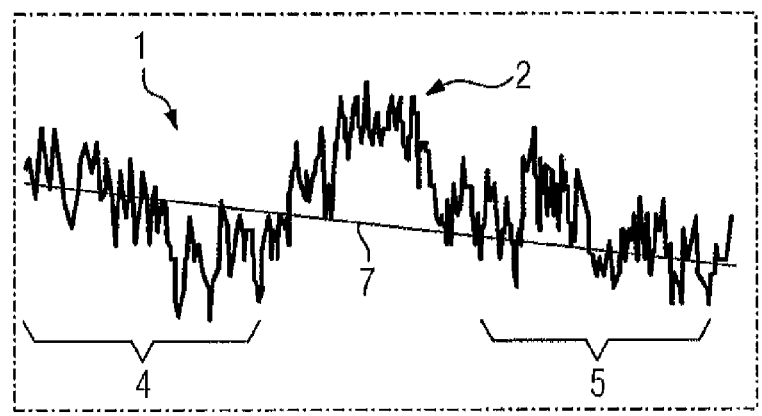
FIGS. 2 to 4 show exemplary graphical plots for approximating a chromatograph for establishing the noise-free baseline.

In a first step a), the chromatogram 1 with the peak 2 of the analyte of interest is produced. FIG. 2 shows the chromatogram 1, from the noise of which the peak 2 protrudes to a greater or lesser extent.

In step b), measured values of the two portions 4 and 5 of the chromatogram 1 in front of and behind the peak 2 of interest are used to calculate by the processor a regression line 7 (y=ax+b) for the noise-free baseline 6.

Figure 3:
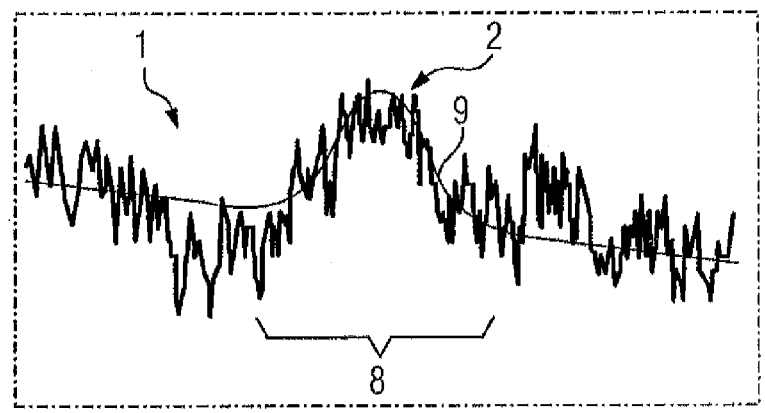

As shown in FIG. 3, a regression function 9 is calculated by the processor in step c) from the measured values of the chromatogram 1 in the region 8 of the peak 2, the regression function 9 consisting of the Gaussian function and the regression line 7. Thus, the regression function 9 is: $y = c \cdot \exp(-((x-d)/e)^2) + ax + b$.

Figure 4:
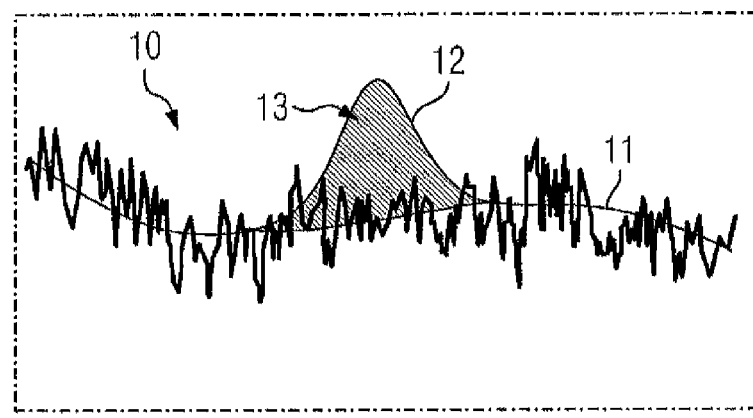

The regression function 9 is subtracted from the chromatogram 1 in step d), and the modified chromatogram 10 without the peak, shown in FIG. 4, is thus obtained.

In step e), a regression polynomial 11 (e.g. $y = fx^3 + gx^2 + hx + i$) for the baseline is calculated by the processor from the values of the chromatogram 10 modified in step d).

In step f), a further regression function 12 is calculated from the measured values of the original chromatogram 1 in the region 8 of the peak 2, with the further regression function 12 consisting of the aforementioned Gaussian function and the regression polynomial 11. Thus, the further regression function 12 is: $y = c \cdot \exp(-((x-d)/e)^2) + fx^3 + gx^2 + hx + i$.

In step g), the peak area 13 between the regression polynomial 11 and the further regression function 12 is calculated in the processor.

Subsequently, step d), with the further regression function 12 in place of the regression function 9, and steps e), f) and g) are repeated until the calculated peak area 13 changes by less than a preset amount. The regression polynomial 11 obtained last approximates the noise-free baseline 6 with great accuracy.

Figure 5:
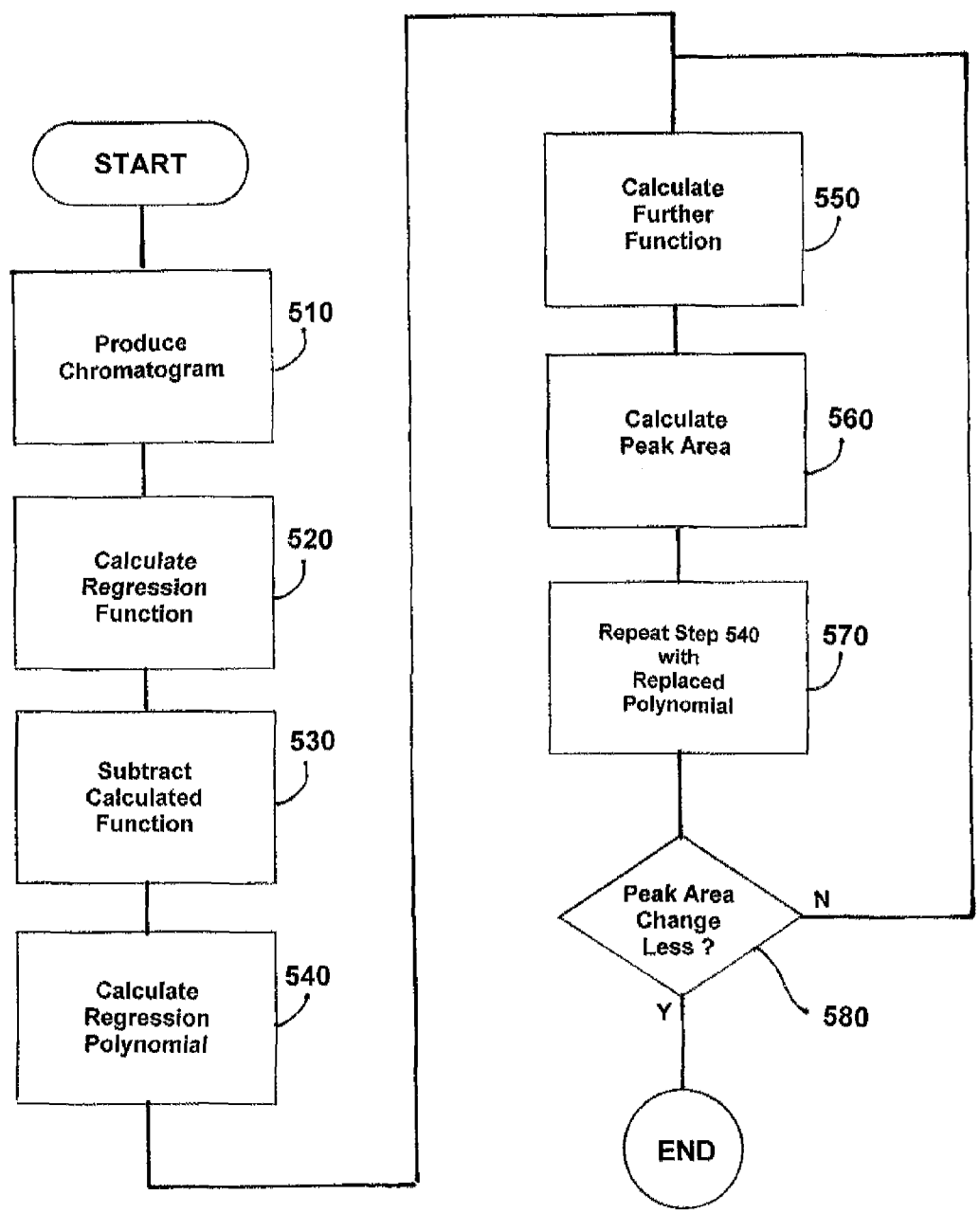
FIG. 5 is a flow chart of the method in accordance with an embodiment of the invention.

FIG. 5 is a flowchart of a method for improving a chromatographic detection limit for an analyte in accordance with the invention. The method comprises producing a chromatogram with a peak of the analyte, as indicated in step 510.

A regression line for a baseline from measured values of a section in the chromatogram without a peak is calculated by a processor, as indicated in step 520.

A regression function is calculated from measured values of the peak of the analyte, as indicated in step 530. Here, the calculated regression function consists of a Gaussian function and the calculated regression line for the baseline.

The calculated regression function is subtracted from the chromatogram, as indicated in step 540.

A regression polynomial for the baseline from values of the chromatogram modified in step 540 is calculated by the processor, as indicated in step 550.

A further regression function is calculated by the processor from the measured values of the peak in the produced chromatogram, as indicated in step 560. Here, the further regression function consists of the Gaussian function and the calculated regression polynomial.

A peak area between the calculated regression polynomial and the calculated further regression function is calculated by the processor, as indicated in step 570.

Step 540 is repeated with the further regression function substituted in place of the calculated regression function, and steps 550, 560, and 570 are repeated until the calculated peak area changes by less than a preset amount, as indicated in step 580.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those method steps which perform substantially the same function in substantially the same way to achieve the same results are within the scope of the invention. Moreover, it should be recognized that method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for improving a chromatographic detection limit for an analyte, comprising:
    a) guiding the analyte through a chromatic separation apparatus;
    b) producing a chromatogram with a peak of the analyte detected by a detector arranged at an outlet of the chromatic separation apparatus;
    c) calculating, by a processor, a regression line for a baseline from measured values of a section in the chromatogram without a peak;
    d) calculating, by the processor, a regression function from measured values of the peak of the analyte, the calculated regression function consisting of a Gaussian function and the calculated regression line for the baseline;
    e) subtracting the calculated regression function from the chromatogram;
    f) calculating, by the processor, a regression polynomial for the baseline from values of the chromatogram modified in step e;
    g) calculating a further regression function from the measured values of the peak in the produced chromatogram, the further regression function consisting of the Gaussian function and the calculated regression polynomial;
    h) calculating, by the processor, a peak area between the calculated regression polynomial and the calculated further regression function;
    i) repeating step e), with the further regression function in place of the calculated regression function, and steps f), g) and h) until the calculated peak area changes by less than a preset amount to generate the improved chromatographic detection limit for the analyte; and
    j) determining a concentration of the analyte based on the calculated peak area.

* * * * *